(12) United States Patent
Griffin

(10) Patent No.: US 6,972,022 B1
(45) Date of Patent: Dec. 6, 2005

(54) SKIN-MARKING DEVICE

(76) Inventor: Michael Griffin, 20717 Prairie St., Chatsworth, CA (US) 91311

( * ) Notice: Subject to any disclaimer, the term of this patent is extended or adjusted under 35 U.S.C. 154(b) by 403 days.

(21) Appl. No.: 10/112,019

(22) Filed: Mar. 27, 2002

(51) Int. Cl.[7] .............................................. A61B 17/00
(52) U.S. Cl. ......................... 606/116; 604/112; 604/260
(58) Field of Search ........................ 606/116, 117, 132, 606/186; 428/40.2, 41.2; 604/111, 112, 115, 604/116, 104, 260, 264, 275; 401/6, 48; 99/345

(56) References Cited

U.S. PATENT DOCUMENTS

| D258,911 S | | 4/1981 | Sandel .......................... D24/23 |
| D264,824 S | | 6/1982 | Sandel .......................... D10/71 |
| D272,421 S | | 1/1984 | Sandel .......................... D10/71 |
| 4,576,163 A | * | 3/1986 | Bliss ............................... 606/1 |
| 4,665,912 A | * | 5/1987 | Burton ......................... 606/185 |
| 4,916,170 A | | 4/1990 | Nambu et al. ............... 523/137 |
| 5,192,270 A | | 3/1993 | Carswell, Jr. ................ 604/116 |
| 5,496,304 A | * | 3/1996 | Chasan ........................... 606/1 |
| 5,665,092 A | * | 9/1997 | Mangiardi et al. ............ 606/86 |
| 5,713,890 A | * | 2/1998 | Chasan ........................... 606/1 |
| 5,743,899 A | | 4/1998 | Zinreich ......................... 606/1 |
| 5,968,479 A | | 10/1999 | Ito et al. ....................... 424/9.6 |
| 6,056,737 A | * | 5/2000 | Rosen ............................. 606/1 |

OTHER PUBLICATIONS

BIC Tri Stic Pens Prior Art Publication Taken From http://store.yahoo.com/1stopshop/bictristic.html dated Feb. 6, 2002 (4 pages).

* cited by examiner

Primary Examiner—Julian W. Woo
Assistant Examiner—Victor Nguyen
(74) Attorney, Agent, or Firm—Cislo & Thomas, LLP

(57) ABSTRACT

A skin-marking device is disclosed that has a holder body and cap having a shape other than round, preferably triangular, to prevent the device from accidentally rolling off a flat surface. Measuring indicia is disposed on the device for accurately measuring distances. The device contains a dermatologically acceptable coloring agent for marking a patient's skin and one that may be selected from the group consisting of a radioopaque substance for x-ray diagnostic purposes, a fluorescent composition, a non-magnetic hydrogel for nuclear magnetic resonance imaging diagnostic purposes, a sterilizable gel ink, a combination of any of these, and a mixture of any of these. The holder body or cap may include a pocket clip or magnet attached thereto to permit the skin marker to be clipped inside a person's pocket or prevented from sliding off a magnetic drape or other magnetic surface, respectively. The skin marker may also come in a number of different sizes, one of which is optionally short enough to allow it to fit into a needle counter box to be packaged as part of a mini kit.

16 Claims, 7 Drawing Sheets ent numeral in one figure will represent the same
SKIN-MARKING DEVICE

BACKGROUND OF THE INVENTION

The field of the present invention relates to medical and surgical tools and particularly to skin-marking devices for marking skin to guide a surgeon in making a proper incision, to aid in diagnostics, or other such similar purposes.

Skin-marking devices are commonly used by the medical industry to color a patient's skin prior to surgery to mark the proper place and length of the incision or incisions to be made during the operation. Skin markers are also commonly used to delineate boundary areas requiring medical therapy or monitoring, such as in conjunction with radiation treatment, or for marking the skin for diagnosis by X-ray tomography and nuclear magnetic resonance imaging.

Skin marking devices in the past have included felt tip pens, magic markers, and other commercially available writing instruments. As time progressed and applications varied, such conventional marking devices have been improved upon. Today, their shape and marking compositions are as varied as they are complex. Examples of today's skin markers include a simple canoe-shaped guide indicia as disclosed in U.S. Pat. No. 4,576,163; a complex marking pin instrument that identifies the precise site, angle, and plane for performing surgery on the spinal column as disclosed in U.S. Pat. No. 5,665,092; a hypodermic syringe provided with a colorant to be placed against the skin after an injection has been given as disclosed in U.S. Pat. No. 5,192,270; a radiation therapy portal area delineation device comprising a template having varied geometric shapes that transfers ink onto the skin in the desired shape as disclosed in U.S. Pat. No. 5,743,899; a single-use pen-like marking device containing a skin fluorescing furanone, activated by breaking a holder containing a solvent that dissolves the furanone as disclosed in U.S. Pat. No. 6,056,737; a vessel, such as a catheter, containing a marking composition for both x-ray tomography and nuclear magnetic resonance imaging as disclosed in U.S. Pat. No. 4,916,170; and a marking pen having a pinwheel at one end for penetrating only the outer layer of the epidermis to deliver a dermatologically acceptable ink for coloring the skin as disclosed in U.S. Pat. No. 5,713,890.

While the above-mentioned devices represent an improvement in the skin-marking field, none of these prior art skin-marking devices are of a shape that precludes them from rolling off flat surfaces. Moreover, these devices do not incorporate measuring indicia for accurately measuring a patient's skin to determine and mark the length of an incision or the like. A skin-marking device having such a non-rollover shape and ruler characteristics is therefore desired. A device that contains a marking substance that is not only dermatologically acceptable but also one that may be used for diagnosis by x-ray tomography and/or nuclear magnetic resonance imaging is even more desired. Finally, such a device containing a gel ink as the marking substance that allows the skin marker to be steam sterilizable, and hence, reusable, is also desired.

SUMMARY OF THE INVENTION

Having recognized these conditions, the present invention is directed to a skin-marking device having a holder body comprised of sidewalls. The sidewalls define a shape of the holder body other than round, preferably triangular, to prevent the skin marker from accidentally rolling off a flat surface. One or more of the sidewalls may have measuring indicia disposed thereon, enabling the device to act as a ruler for accurately measuring distances. More preferably, a cap adapted to fit over a portion of the holder body has measuring indicia disposed thereon. In this manner, a surgeon may accurately measure distances with the cap and then conveniently and efficiently mark those distances.

The sidewalls may also define a channel or reservoir for holding a coloring agent for marking a patient's skin. The coloring agent is a dermatologically acceptable composition and one that is also preferably selected from the group consisting of a radioopaque substance for x-ray diagnostic purposes, a fluorescent composition, a non-magnetic hydrogel for nuclear magnetic resonance imaging diagnostic purposes, a sterilizable gel ink, a combination of any of these, and a mixture of any of these. If the end application of the skin-marking device is for x-ray diagnostic purposes, the holder body and cap are also preferably made of a radioopaque substance.

The holder body may optionally include a pocket clip or magnet attached thereto. In the alternative, a pocket clip or magnet may be disposed on the cap, depending on the cap's length. In this manner, the skin marker can be advantageously clipped inside a person's pocket or prevented from sliding off a magnetic drape or other magnetic surface, respectively.

The skin marker may also come in a number of different sizes, one of which is optionally short enough to allow it to fit into a needle counter box. Such an advantage allows minimal packaging when the two items are used in a small medical kit or mini kit. Other and further objects and advantages will appear hereinafter.

DETAILED DESCRIPTION OF PREFERRED EMBODIMENTS

Preferred embodiments will now be described with reference to the drawings. For clarity of description, any element numeral in one figure will represent the same element if used in any other figure.

Figure 1:
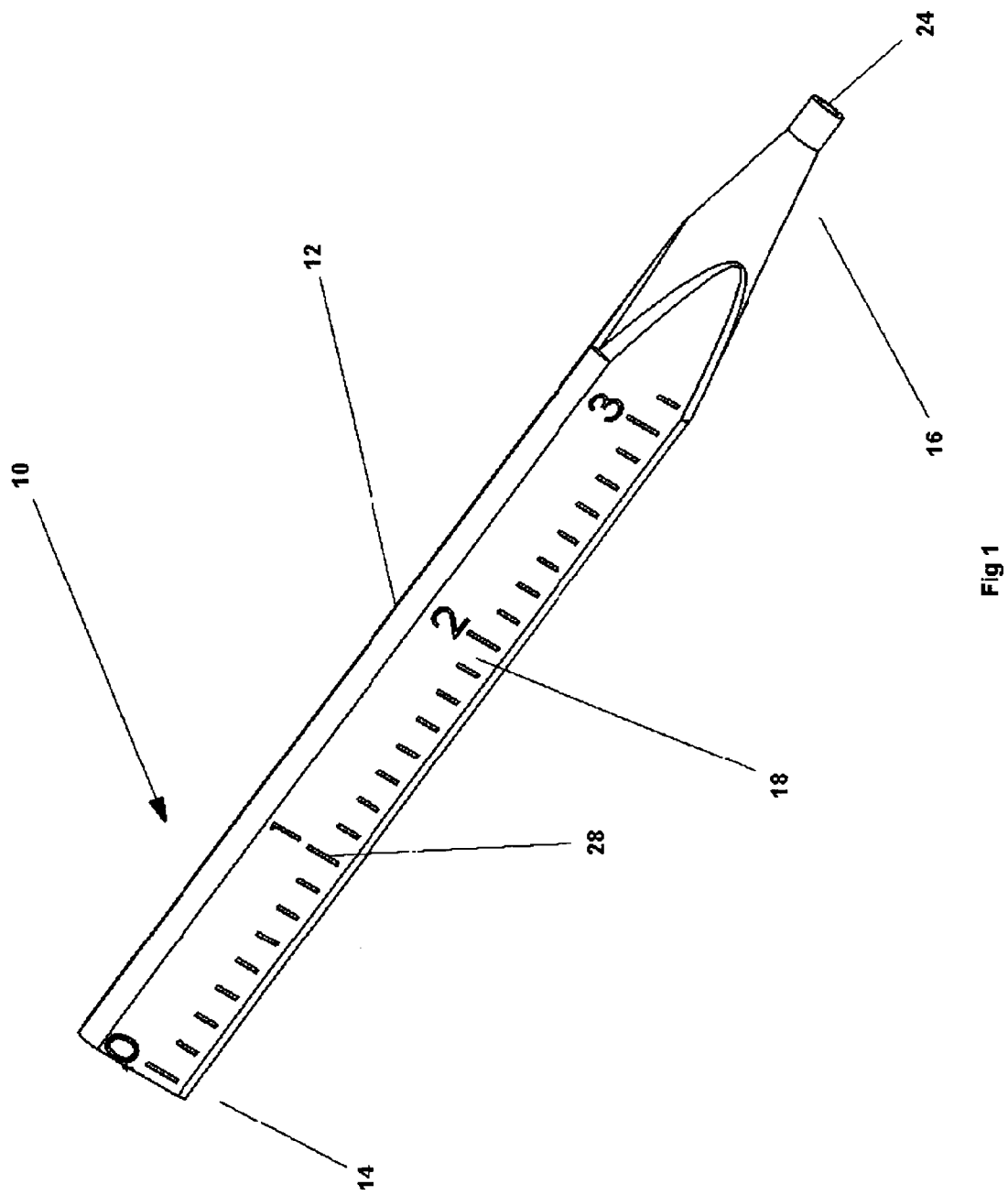
FIG. 1 is a perspective view of a skin-marking device according to a first preferred embodiment.

FIG. 1 illustrates a skin-marking device 10 having a top end 14 and a bottom end 16. The device 10 comprises a holder body 12. The holder body 12 is defined by sidewalls 18. The sidewalls 18 define a channel or reservoir 20 located in the central portion of the skin marker 10, as shown in FIG. 2.

Figure 2:
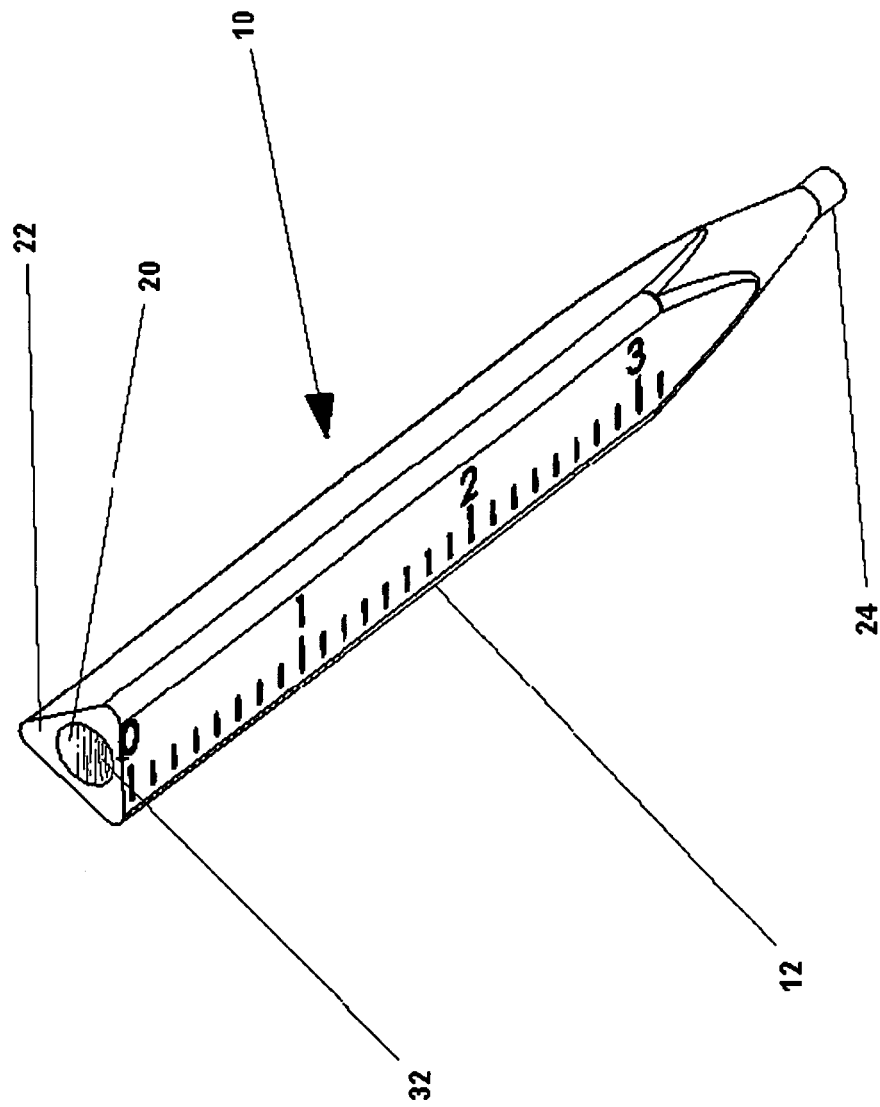
FIG. 2 is a perspective view of the skin-marking device shown in FIG. 1.

At the top end 14 of the device 10, a cap 26 may be disposed for helping contain fluid 32 or the like held within the reservoir 20, as illustrated in FIGS. 1 and 2. Similarly, a nib holder 24 may be disposed at the other end 16 of the device 10 for keeping fluid 32 within the reservoir 20. Detailed views of the cap 26 and nib holder 24 are illustrated in FIGS. 4 and 5, respectively, and are discussed in detail below.

Should the present invention comprise the nib holder 24 and cap 26 arrangement as illustrated in FIGS. 1 and 2, the holder body 12 may have a ledge 22 or the like at both the top and bottom ends 14, 16 for seating purposes. The ledge 22, as the name implies, is a flat surface, upon which a complimentary flat surface of the nib holder 24 or cap 26 may be frictionally seated.

Figure 4:
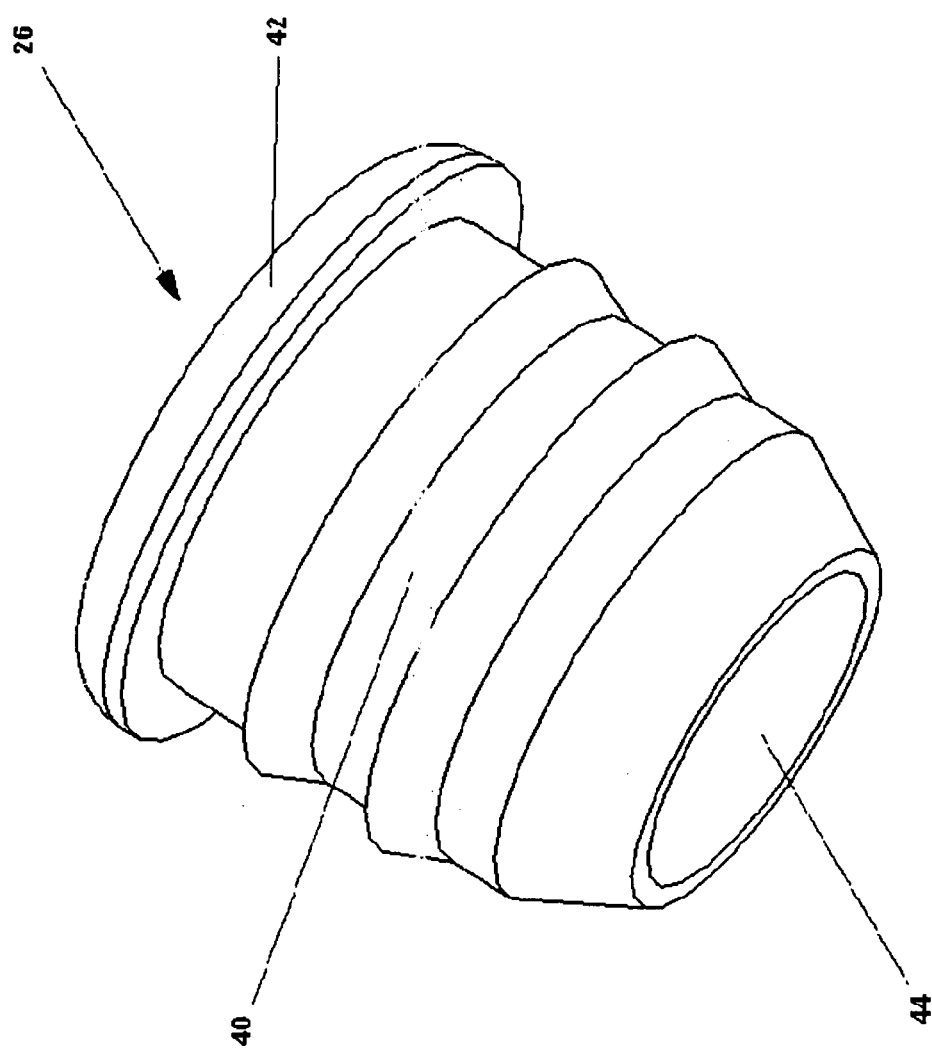
FIG. 4 is a perspective, detailed view of a cap used in a skin-marking device according to the preferred embodiments.
Figure 5:
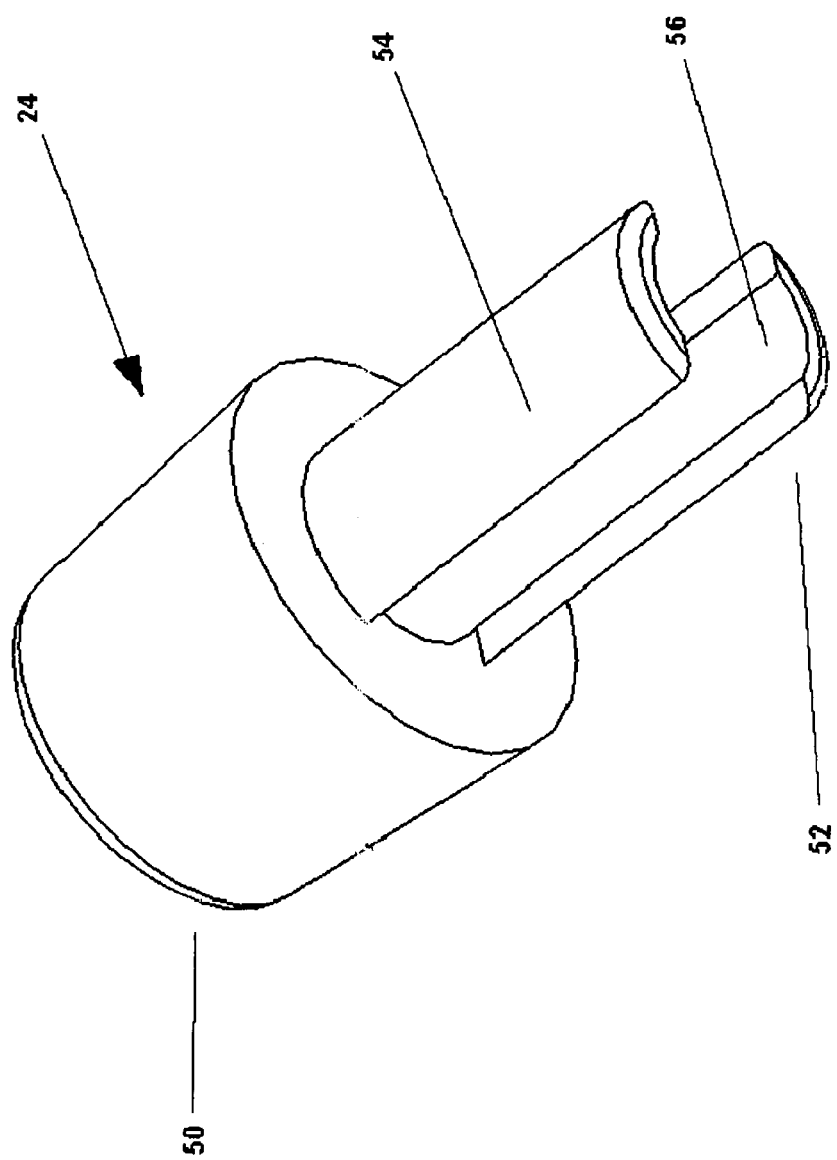
FIG. 5 is a perspective, detailed view of the nib holder shown in FIGS. 1 and 2.

In particular, as shown in FIG. 4, cap 26 comprises a cylindrically shaped object defined by ribbed sidewalls 40 and a top wall 42. The circumference of the sidewalls 40 is designed to be inserted into the top end 14 and then frictionally engage the sidewalls 18 of the holder body 12, thereby capping off reservoir 20 at the top end 14. The top wall 42 is dimensioned to overlap ledge 22, and should be of a height to allow for easy gripping of cap 26 for ink 32 changing or replacement.

In like manner, nib holder 24 is designed for frictional engagement with the opening of reservoir 20 at the bottom end 16 of the holder body 12. In particular, nib holder 24 comprises a top end 50 and bottom end 52 defined by sidewalls 54. Sidewalls 54 may define a channel 56 for receiving a tube or the like. Should this arrangement be employed, a tube (not shown) may actually contain the marking substance 32, and may be disposable once the marking substance 32 has been depleted. To accommodate the tube at the other end 14 of the holder body 12, cap 26 may also include a channel 44 for snugly receiving the diameter of the tube. In the alternative, nib holder 24 may actually comprise the nib or applicator itself and/or the nib may be pushed into the holder body 12 such that there may not be a need for a nib holder 24. With this alternate arrangement, the applicator 24 is preferably a felt-like substance similar to that found in commercially available felt-tip pens, permitting the marking substance or ink 32 to be absorbed from the reservoir 32 and then applied onto the patient's skin, in the same manner as a commercially available felt-tip pen would be used.

Figure 3:
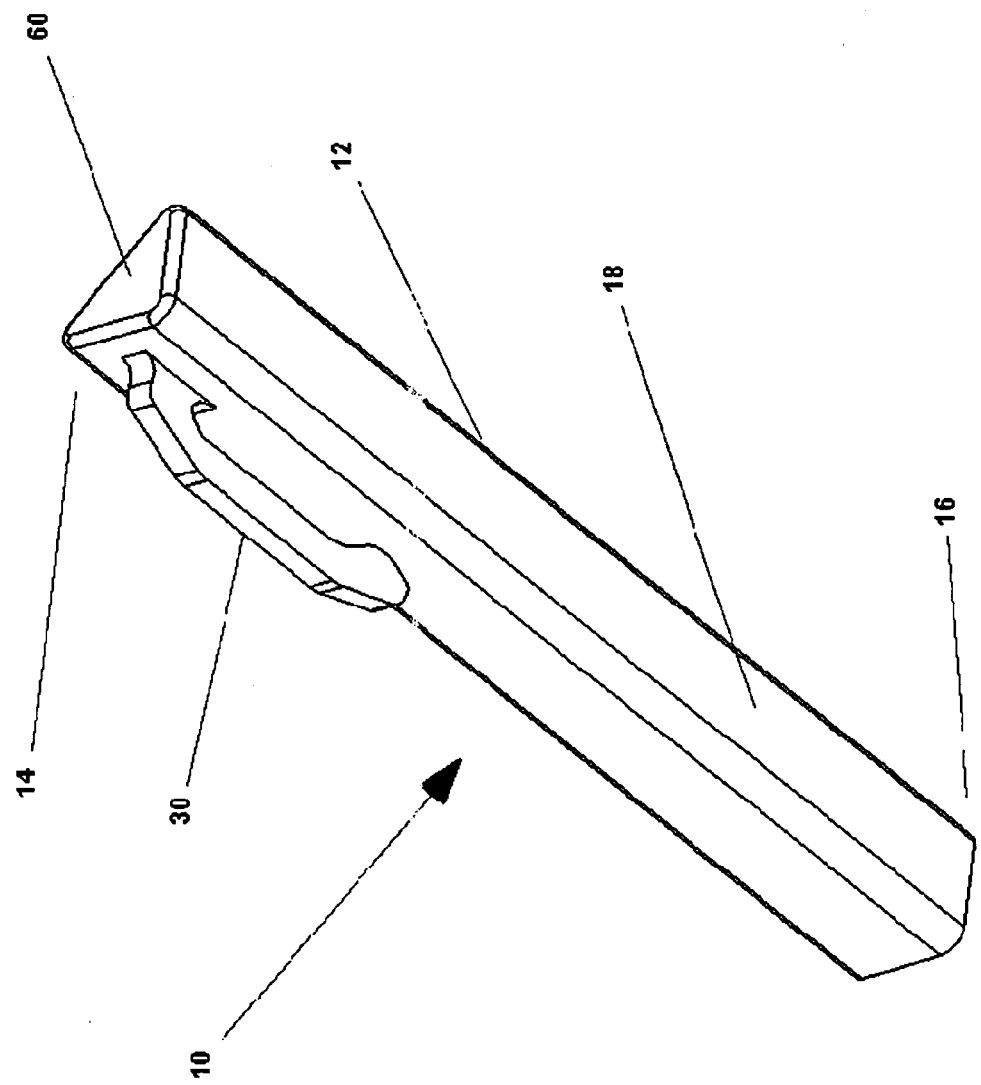
FIG. 3 is a perspective view of a skin-marking device according to a second preferred embodiment.

Instead of the nib 24 and cap 26 arrangement, the skin marker 10 may have a holder body that has an opening at only the bottom end 16. In this manner, the skin marker 10 would not only have sidewalls 18 but also a top wall 60, as illustrated in FIG. 3. The bottom end 16 may be enclosed via a cap 26 or the like, depending on the end application. Such a design may advantageously be less costly to manufacture, involving at least one less part and economical injection-molding processes. This design may be best used for a skin marker 10 that is not reusable, as it may be more difficult to resupply the reservoir 20 with ink 32 when depleted.

The shape of the skin marker 10 is one other than round to prevent the device 10 from accidentally rolling of flat surfaces. Preferably, the shape is triangular as illustrated in FIGS. 1–3 and 6–7. Such a triangular shape is not only functionally advantageous, but it is also ergonomic in that it provides a comfortable fit within one's hand.

The present invention is particularly adapted for use as a surgical or medical tool for coloring a patient's skin prior to surgery, marking skin for diagnostic purposes involving x-ray tomography and/or nuclear magnetic resonance imaging, delineating boundary areas requiring medical therapy or monitoring, such as in conjunction with radiation treatment, or the like. Accordingly, the fluid 32 contained in reservoir 20 should be dermatologically acceptable for coloring a patient's skin. "Dermatologically acceptable", as used herein, generally refers to an ink that is substantially permanent or indelible while remaining non-toxic. Suitable examples of such coloring materials may include iodine, mercurochrome or methiolate, food colorings and the like. These dermatologically acceptable ink compositions or substances are distinguished from the harmful and deleterious toxins contained in conventionally known writing devices that surgeons may have used in the past, such as magic markers and commercially available felt-tip pens.

The dermatologically acceptable coloring agent 32 is also preferably selected from the group consisting of a radioopaque substance for x-ray diagnostic purposes, a non-magnetic hydrogel for nuclear magnetic resonance imaging diagnostic purposes, a sterilizable gel ink, a fluorescent composition, a combination of any of these, and a mixture of any of these.

A suitable composition for both x-ray tomography and nuclear magnetic resonance imaging diagnostic purposes is disclosed in U.S. Pat. No. 4,916,170 issued to Nambu et al., hereby incorporated by reference as if fully set forth herein. As disclosed in Nambu, the skin marker composition that may be employed in the preferred embodiments of the instant invention may be comprised of a radioopaque material for x-ray diagnostic purposes and/or a non-magnetic hydrogel for magnetic resonance 110 imaging purposes. If the end application of the skin-marking device is for x-ray diagnostic purposes, the holder body 12 and cap 26 should also be made of a radioopaque substance.

If the device 10 contains a gel ink as the marking substance 32, the skin marker 110 may be steam sterilizable. Such a gel ink marker composition 32 would advantageously allow the marker 10 to be reusable.

If the device 10 contains a fluorescent composition as the marking substance 32, a fluorogenically-effective concentration of a furanone, preferably fluorescamine, dissolved in an appropriate carrier fluid such as ethanol, DMF or DMSO, may be employed. Such a fluorescent marker composition 32 would advantageously allow the marker 10 to mark skin with marks that are visible under ultra-violet light only, i.e., assuming the marks are durable enough to remain on the patient for one or more days, the marks would not be cosmetically unappealing and perhaps psychologically detrimental to the patient.

As illustrated in FIG. 1, at least one of the sidewalls 18 of the holder body 12 may include measuring indicia 28 disposed thereon. The measuring indicia 28, particularly when combined with the preferred triangular shape defining three flat surfaces, advantageously permits the user to accurately measure distances. In this manner, the marking device 10 effectively permits a surgeon to use the instrument 10 as a ruler to accurately determine the length of a desired incision before coloring the patient's skin, or the like. In addition, with each flat surface, different ruler scales may be employed as the measuring indicia 28. For example, with the preferred triangular shape, such ruler scales may comprise English measurements, metric measurements, and a combination of both English and metric measurements, respectively.

Figure 6:
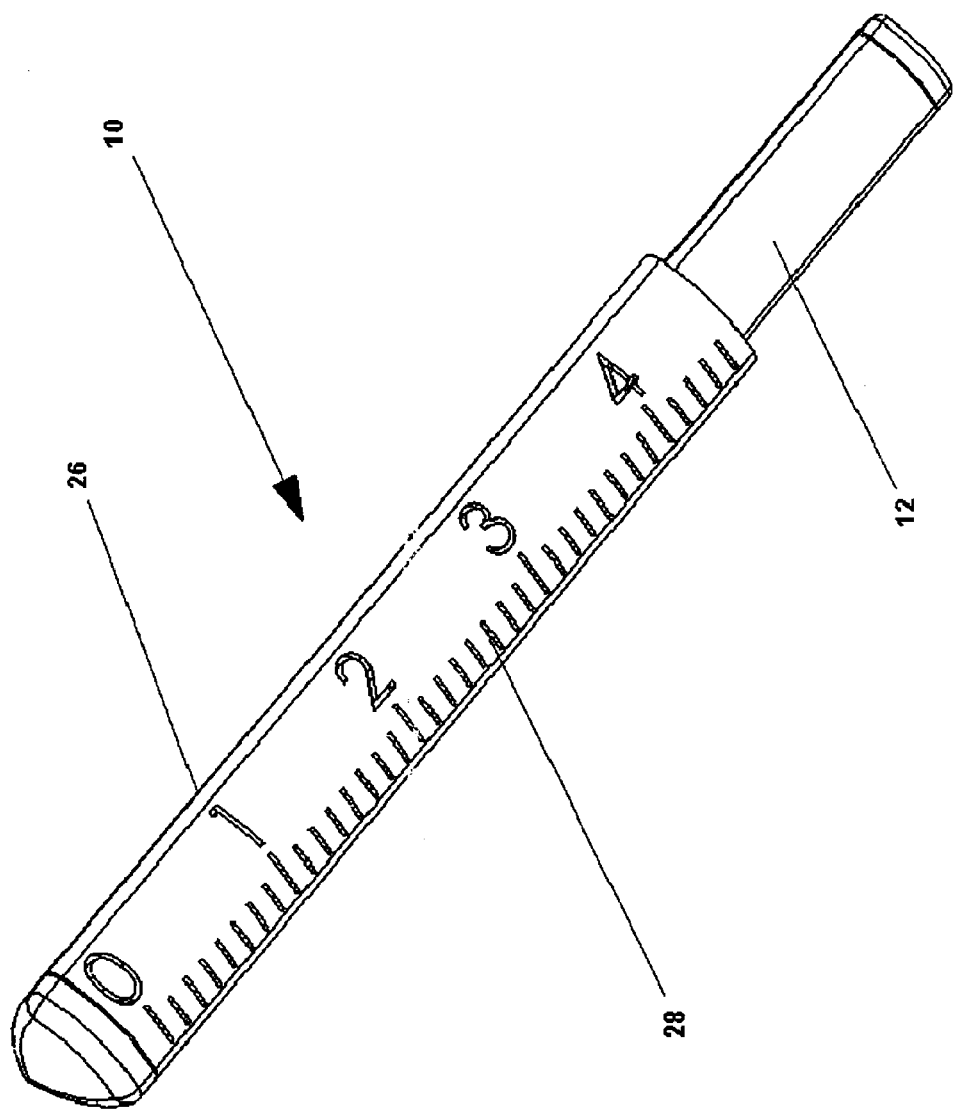
FIG. 6 is a perspective view of a skin-marking device according to another preferred embodiment.
Figure 7:
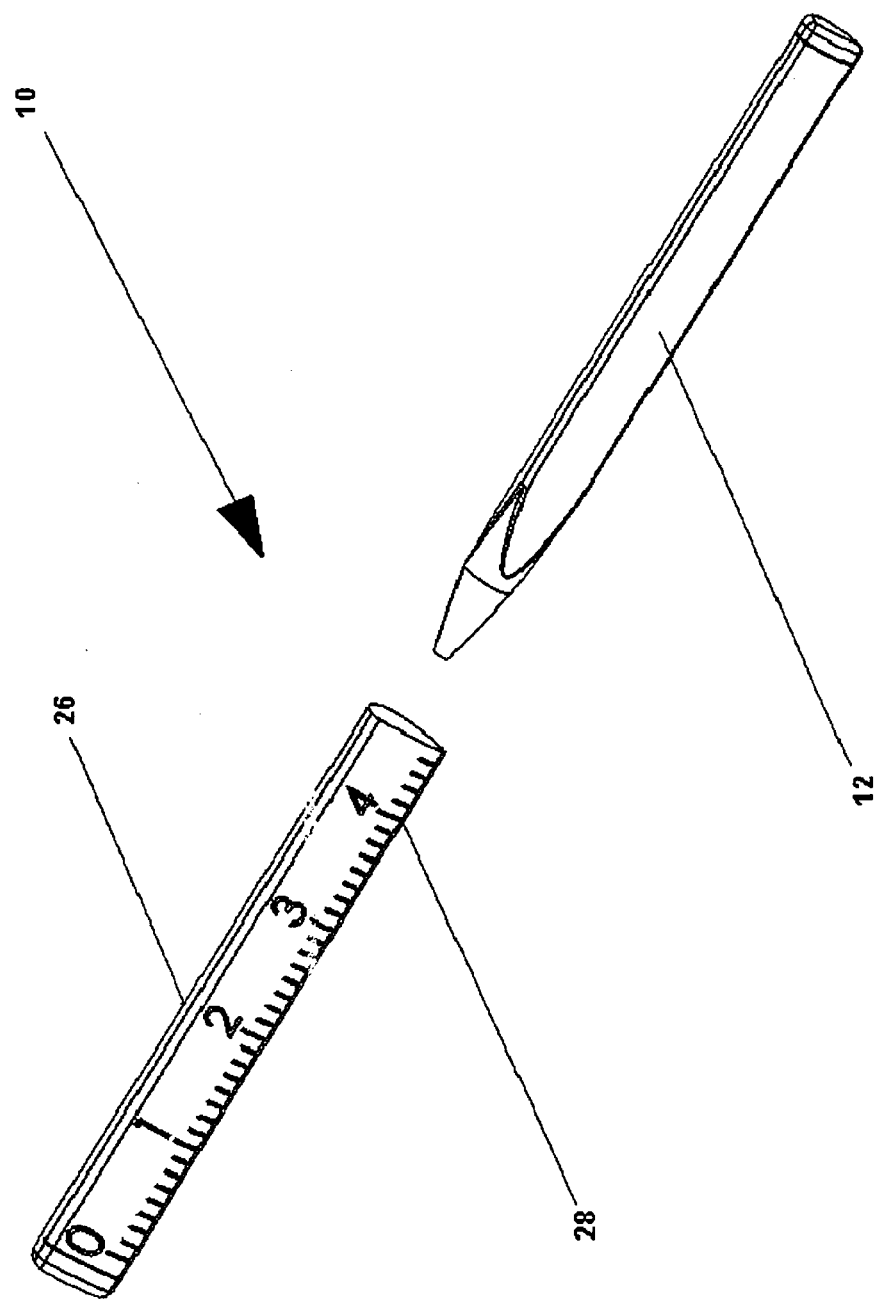
FIG. 7 is a perspective view of the skin-marking device shown in FIG. 6, illustrating the cap disassociated from the holder body.

FIGS. 6 and 7 illustrate the measuring indicia 28 may be more preferably disposed on the cap 26 associated with the holder body 12. With this arrangement, a surgeon may advantageously accurately measure distances with the cap 26 and then mark those distances with the coloring agent 32 contained in the holder body 12. As seen in these drawing figures, both the cap 26 and holder body 12 are preferably triangular in shape to prevent inadvertent and/or undesirable rolling of these objects.

The holder body 12 preferably includes a pocket clip 30, as illustrated in FIG. 3, to permit the skin marker 10 to be clipped inside a person's pocket. Alternatively, or perhaps in combination with the pocket clip 30, the holder body 12 may include a magnet (not shown) attached thereto to prevent the skin marker 10 from sliding off a magnetic drape or other magnetic surface. Although not shown in FIGS. 6 and 7, the pocket clip 30 may alternatively be disposed on the cap 26, depending on the cap's length.

The skin marker 10 may also come in a number of different sizes, one of which is optionally short enough to allow it to fit into a needle counter box. Such a design advantageously allows for minimal packaging when the two items are used in a small medical kit or mini kit.

The skin marker 10 may also include a pinwheel (not shown) rotatably mounted to the bottom end 16 of the holder body 12. The pinwheel is preferably of a design to permit coloring of the patient's skin by penetrating only the outer layer of the epidermis, thereby improving the duration that the skin will remain colored, without permanently tattooing the skin.

Thus, while embodiments and applications of the improved skin-marking device have been shown and described, it would be apparent to one skilled in the art that other modifications are possible without departing from the inventive concepts herein. The invention, therefore, is not to be restricted except in the spirit of the claims that follow.

What is claimed is:

1. A skin-marking device, comprising:
   a body having at least one substantially flat side and at least one internal channel, said at least one internal channel being defined by at least one wall;
   a dermatologically acceptable coloring agent being in direct contact with said at least one wall of said at least one internal channel, said coloring agent being used to mark a patient's skin;
   at least one distance measuring indicia on said at least one substantially flat side of said body; and
   a nib portion operatively coupled to said at least one internal channel of said body and adapted to apply the coloring agent onto the patient's skin.

2. The skin-marking device of claim 1, wherein said body has a substantially triangular cross-section.

3. The skin-marking device of claim 2, wherein at least two sides of said body are provided with distance measuring indicia.

4. The skin-marking device of claim 2, wherein at least one side of said body is provided with a metric scale.

5. The skin-marking device of claim 2, wherein at least one side of said body is provided with a British measurement scale.

6. The skin-marking device of claim 2, wherein the size of said body is configured to fit into a needle counter box.

7. The skin-marking device of claim 1, wherein said at least one internal channel has a substantially circular cross-section.

8. The skin-marking device of claim 1, wherein said dermatologically acceptable coloring agent comprises a radioopaque substance for X-ray diagnostic purposes.

9. The skin-marking device of claim 8, wherein said body is made of a radioopaque substance for X-ray diagnostic purposes.

10. The skin-marking device of claim 1, wherein said dermatologically acceptable coloring agent comprises a non-magnetic hydrogel for nuclear magnetic resonance imaging.

11. The skin-marking device of claim 1, wherein said dermatologically acceptable coloring agent comprises a sterilizable gel ink.

12. The skin-marking device of claim 1, wherein said dermatologically acceptable coloring agent comprises a fluorescent composition.

13. The skin-marking device of claim 1, wherein said dermatologically acceptable coloring agent includes iodine.

14. The skin-marking device of claim 1, wherein said dermatologically acceptable coloring agent includes mercurochrome.

15. The skin-marking device of claim 1, wherein said dermatologically acceptable coloring agent includes methiolate.

16. The skin-marking device of claim 1, wherein said dermatologically acceptable coloring agent includes food coloring.

* * * * *